(12) United States Patent
Roche et al.

(10) Patent No.: US 10,564,084 B2
(45) Date of Patent: Feb. 18, 2020

(54) RAPID CHARACTERIZATION OF THE SOLUBILITY OF AMPHIPHILES

(71) Applicants: The Trustees of Princeton University, Princeton, NJ (US); CNRS-Centre National De La Recherche Scientifique, Paris (FR); Universite De Rennes I, Rennes (FR); The Chancellor, Masters and Scholars of the University of Oxford, Oxford, Oxfordshire (GB)

(72) Inventors: Matthieu Roche, Paris (FR); Howard A. Stone, Princeton, NJ (US); Isabelle Cantat, Rennes (FR); Arnaud Saint-Jalmes, Cesson Sevigne (FR); Ian Griffiths, Oxford (GB); Sebastien Le Roux, Brest (FR); Zhen Zhen Li, Paris (FR)

(73) Assignees: THE TRUSTEES OF PRINCETON UNIVERSITY, Princton, NJ (US); CNRS-CENTRE NATIONAL DE LA RECHERCHE SCIENTIFIQUE, Paris (FR); UNIVERSITE DE RENNES I, Rennes (FR); CHANCELLOR, MASTERS & SCHOLARS OF UNIV. OF OXFORD, Oxford (GB)

( * ) Notice: Subject to any disclaimer, the term of this patent is extended or adjusted under 35 U.S.C. 154(b) by 1234 days.

(21) Appl. No.: 14/764,719
(22) PCT Filed: Jan. 30, 2014
(86) PCT No.: PCT/EP2014/051856
§ 371 (c)(1),
(2) Date: Jul. 30, 2015
(87) PCT Pub. No.: WO2014/118303
PCT Pub. Date: Aug. 7, 2014

(65) Prior Publication Data
US 2015/0355065 A1 Dec. 10, 2015

Related U.S. Application Data

(60) Provisional application No. 61/759,459, filed on Feb. 1, 2013.

(51) Int. Cl.
*G01P 3/36* (2006.01)
*G01N 13/02* (2006.01)
*G01N 15/00* (2006.01)

(52) U.S. Cl.
CPC ..... *G01N 13/02* (2013.01); *G01N 2013/0275* (2013.01); *G01N 2013/0283* (2013.01); *G01N 2015/0003* (2013.01)

(58) Field of Classification Search
CPC ............ G01N 13/02; G01N 33/491; G01N 2013/0275; G01N 2013/0283
(Continued)

(56) References Cited

U.S. PATENT DOCUMENTS

2015/0118696 A1* 4/2015 Haselton .......... G01N 33/54306
435/7.92

OTHER PUBLICATIONS

International Search Report for PCT/EP2014/051856 dated Apr. 16, 2014.
(Continued)

*Primary Examiner* — Mark Hellner
(74) *Attorney, Agent, or Firm* — Thomas | Horstemeyer, LLP

(57) ABSTRACT

Disclosed is a process and device allowing for fast measurements of the physicochemical properties of amphiphiles (lipids, surfactants, soaps, . . . ). A Marangoni flow is created and characterized using amphiphiles to be characterized. The observed flow is characterized, and using the disclosed process, one can deduce from this measurement many important physicochemical parameters of the amphiphiles such as their critical micellar concentration. Compared to existing techniques, the disclosed process offers the advantage that it requires a single experiment to deduce the parameters, when other techniques (pendant drop method, conductometry, etc . . . ) require the measurement of a quantity (interfacial tension, conductometry) against a (Continued)

systematically varied parameter (amphiphile concentration, . . . ). The disclosed process and devices are ideal to characterize and/or screen rapidly amphiphiles molecules based on their interaction with a solvent.

18 Claims, 11 Drawing Sheets

(58) Field of Classification Search
USPC .......................................................... 356/28
See application file for complete search history.

(56) References Cited

OTHER PUBLICATIONS

Roche Matthieu: "Surfactant-assisted spreading of an oil-in-water emulsion on the surface of a liquid bath", , Oct. 18, 2010 (Oct. 18, 2010), XP054975369, Retrieved from the Internet: URL:http://arxiv.org/abs/1010.3236 [retrieved on Apr. 4, 2014].

D.G Suciu et al: "The spreading of liquids on liquids", Journal of Colloid and Interface Science, vol. 33, No. 4, Aug. 1, 1970 (Aug. 1, 1970), pp. 520-528, XP055109510, ISSN: 0021-9797, DOI: 10.1016/0021-9797 (70)90003-2.

D. G. Suciu et al: "Some experiments on the Marangoni effect", AICHE Journal, vol. 13, No. 6, Nov. 1, 1967 (Nov. 1, 1967), pp. 1120-1124, XP055109513, ISSN: 0001-1541, DOI: 10.1002/aic.690130616.

E. Ruckenstein et al: "A steady dissolving drop method for studying the pure Marangoni effect", Chemical Engineering Science, vol. 25, No. 8, Aug. 1, 1970 (Aug. 1, 1970), pp. 1249-1254, XP055109505, ISSN: 0009-2509, DOI: 10.1016/0009-2509(70)80001-X.

D G Suciu et al: "On the Structure of Dissolving Thin Liquid Films", AL CH E, vol. 15, No. 5, Jan. 1, 1969 (Jan. 1, 1969), pp. 686-689, XP055109855.

\* cited by examiner

RAPID CHARACTERIZATION OF THE SOLUBILITY OF AMPHIPHILES

CROSS-REFERENCE TO RELATED APPLICATION

This application is the 35 U.S.C. § 371 national stage application of PCT Application No. PCT/EP2014/051856, filed Jan. 30, 2014, which claims priority to and the benefit of, U.S. Provisional Application No. 62/759,459, filed Feb. 1, 2013, both of which are herein incorporated by reference in their entirety.

FIELD OF THE INVENTION

The present invention relates to a method, and device thereof, for assessing the solubility of amphiphilic compounds in a solvent. The present invention is particularly suitable for measuring different physicochemical parameters, such as the critical micellar concentration, of said amphiphilic compounds. It relies on the spreading behavior of an amphiphilic compound at the interface between a solvent and air, so that the physicochemical properties of an amphiphilic compound is assessed based on the characterization of the spreading flow induced by the said amphiphilic molecules and observed at the surface of the said solvent. The present invention allows assessing the solubility of amphiphilic compounds in a reliable, simple, objective and rapid way. Particularly, the present invention allows assessing a specific physicochemical parameter, such as the critical micellar concentration, by performing a single large-scale measurement step.

BACKGROUND OF THE INVENTION

Various methods have been developed so far for measuring the physicochemical properties of amphiphilic compounds, including the diffusion constants or the critical micellar concentration. Existing measurement methods, also referred as equilibrium techniques, require measuring the complete variation of a first parameter (e.g. the surface tension, interfacial tension, conductometry) against a second parameter (e.g. the concentration of amphiphilic compounds in water). Existing methods are, for example, the pendant drop method or the conductometry method. These relative measurements of one parameter versus another are usually time-consuming, as it may take up to many full days for measuring the physicochemical parameter of interest.

FIGURES

Figure 1A:
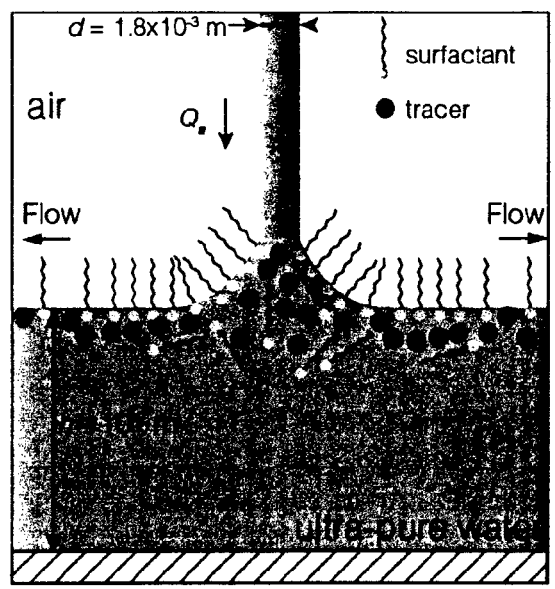
FIG. 1a is a schematic representation of the step of injecting the traceable solution at the surface of the solvent layer.
Figure 1B:
FIG. 1b is a photographic side view of the top surface of the solvent layer, during injection of the traceable solution.
Figure 1C:
FIG. 1c is a photographic top view of the top surface of the solvent layer, during injection of the traceable solution.
Figure 1D:
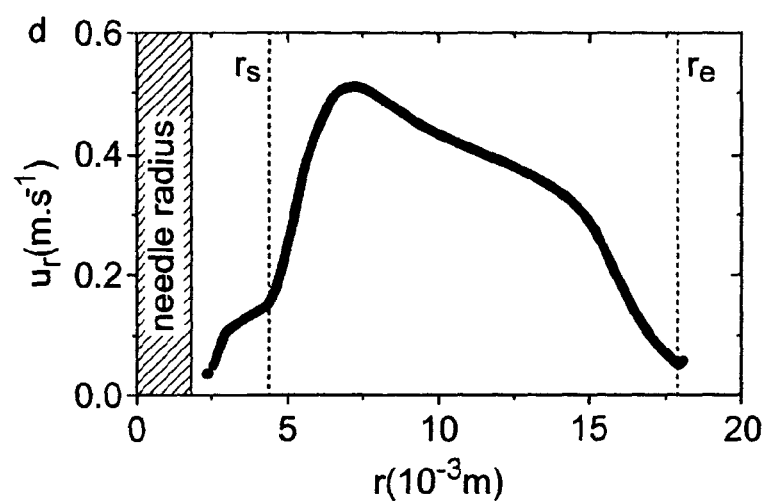
Figure 2A:
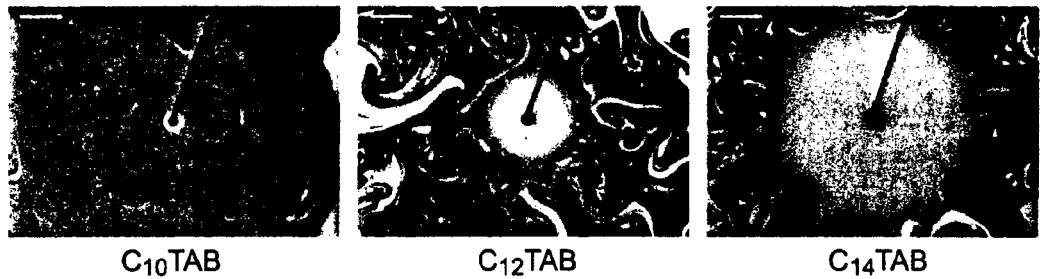

FIG. 1d is a graphic of the velocity field $u_r$ (m·s$^{-1}$) as a function of the radius r ($10^{-3}$ m) of the flow regions FIG. 2a is three photographic top views of the top surface of the solvent layer, during injection of traceable solutions comprising three different surfactants, namely $C_{10}$ trimethyl ammonium bromide ($C_{10}$TAB), $C_{12}$ trimethyl ammonium bromide ($C_{12}$TAB), and $C_{14}$ trimethyl ammonium bromide ($C_{14}$TAB).

Figure 2B:
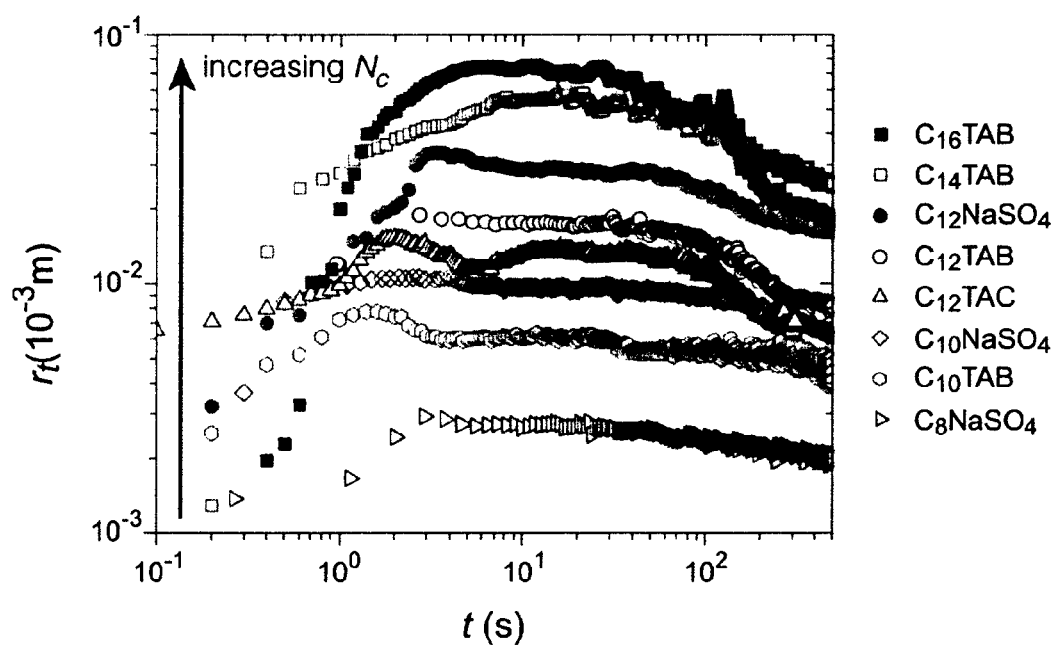

FIG. 2b is a graphic representation of the measurement of the radius $r_e$ of the transparent zone $r_e$ ($10^{-3}$ m) as a function of time t (s), for surfactants HTAC, TTAB, SDS, DoTAB, DoTAC, SDeS, DeTAB and SOS ($Q_a$=0.52×10$^{-6}$ mol·s$^{-1}$, c=260×10$^{-3}$M).

Figure 2C:
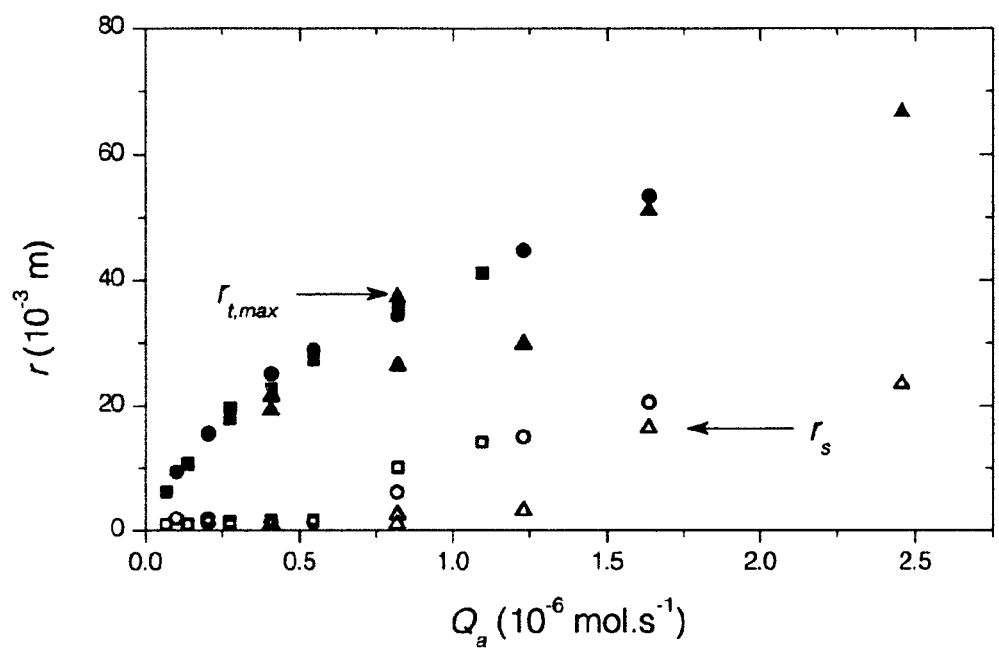

FIG. 2c is a graphic representation of the radius $r_e$ ($10^{-3}$ m) as a function of the surfactant flow rate $Q_a$ ($10^{-6}$ mol·s$^{-1}$) for SDS (θ=0.4, [SDS]=260×10$^{-3}$M).

Figure 3A:
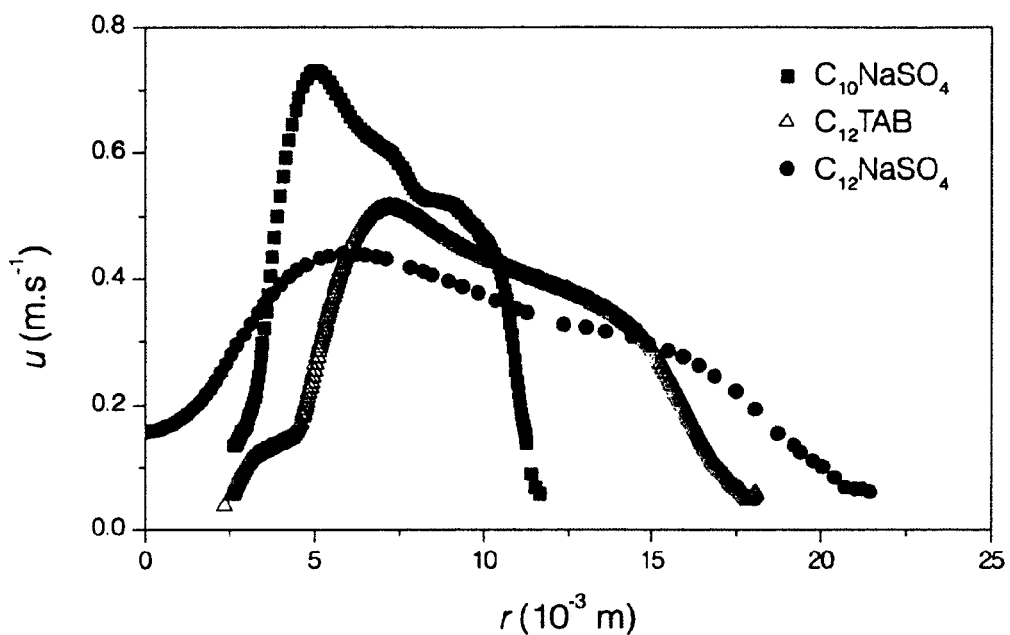

FIG. 3a is a graphic representation of the velocity $u_r$ (m·s$^{-1}$) as a function of the radius ($10^{-3}$ m), at constant flow rate, for surfactants SDeS, DoTAB, and SDS ($Q_a$=0.52×10$^{-6}$ mol·s$^{-1}$).

Figure 3B:
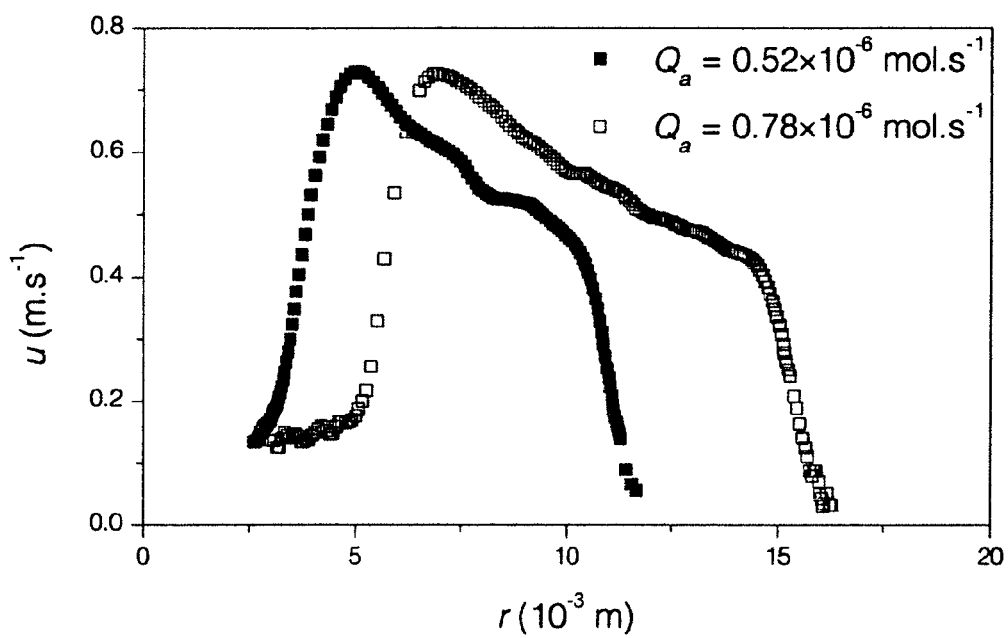

FIG. 3b is a graphic representation of the velocity $u_r$ (m·s$^{-1}$) as a function of the radius r ($10^{-3}$ m), for surfactant SDeS, at different flow rate.

Figure 4A:
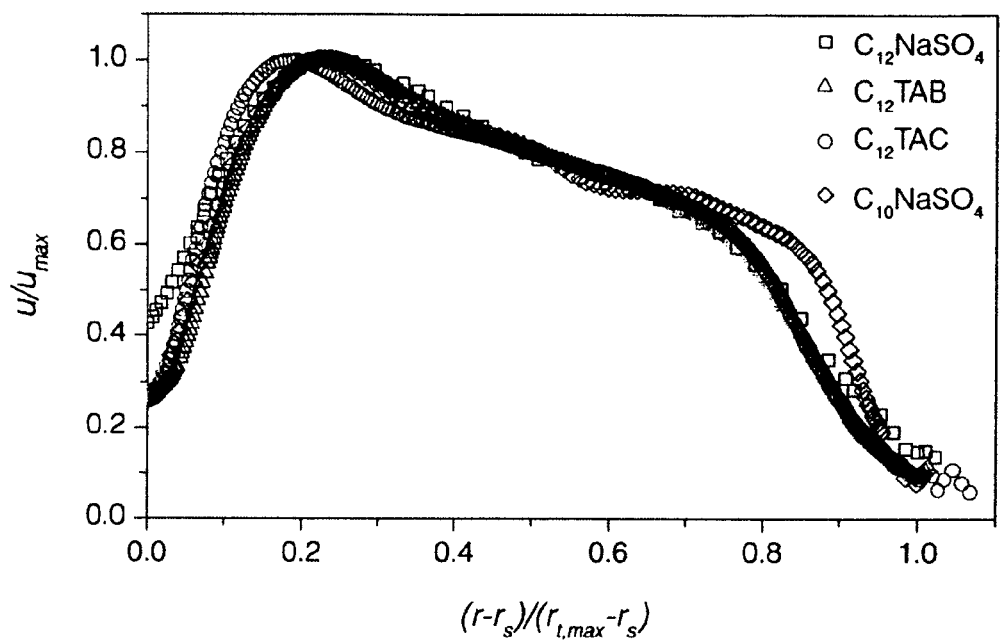

FIG. 4a is a graphic representation of the velocity profiles normalized by the maximum magnitude of the velocity $U=u/u_{max}$ and it shows the position of the boundaries of the source and the transparent zone $R=(r-r_s)/(r_e-r_s)$, for surfactants SDS, DoTAB, DoTAC and SDeS.

Figure 4B:
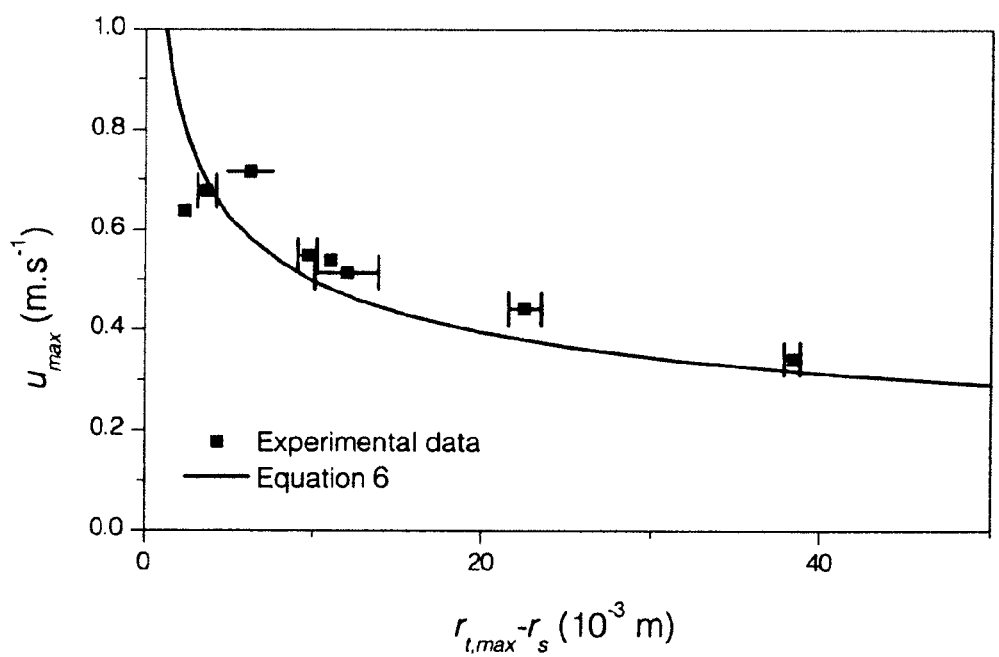

FIG. 4b is a graphic representation comparing the equation (6) and the experimental data for the maximum velocity $u_{max}$ (m·s$^{-1}$) as a function of $r_{t,max}-r_s$ ($10^{-3}$ m).

Figure 4C:
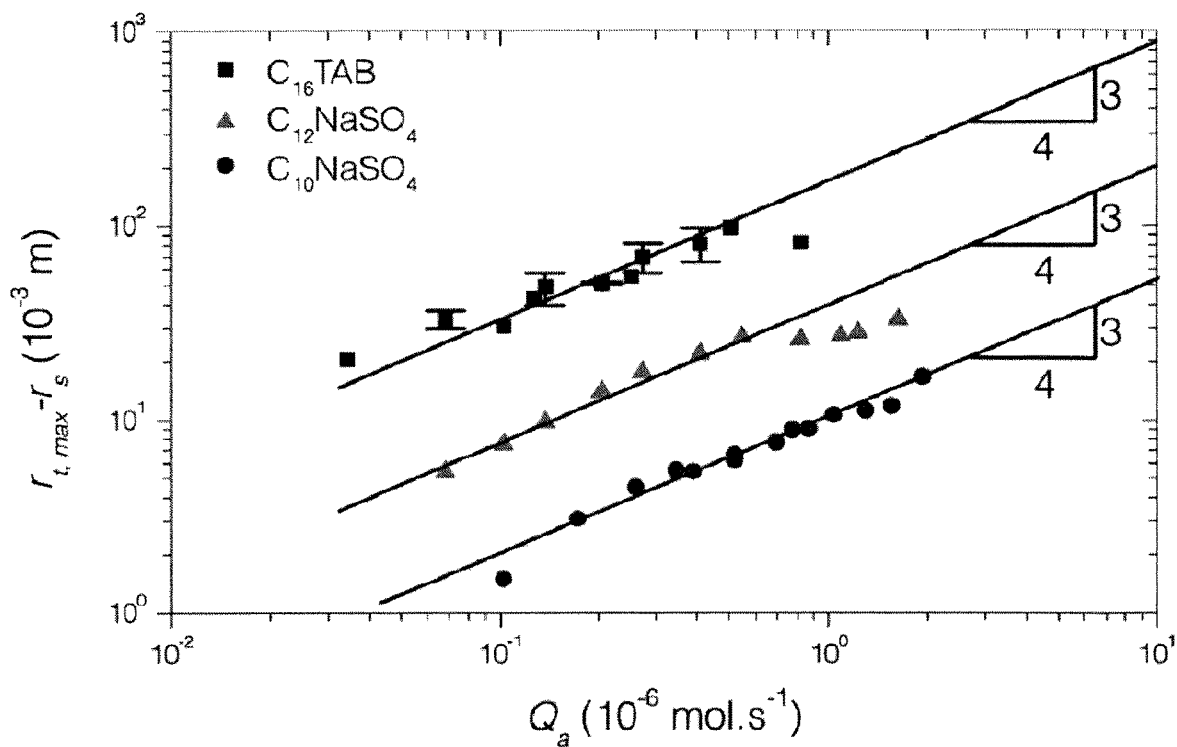

FIG. 4c is a graphic representation comparing the equation (7) and the experimental data for the maximal size of the transparent zone $r_{t,max}-r_s$ ($10^{-3}$ m) as a function of the surfactant molar flow rate $Q_a$ ($10^{-6}$ mol·s$^{-1}$).

Figure 4D:
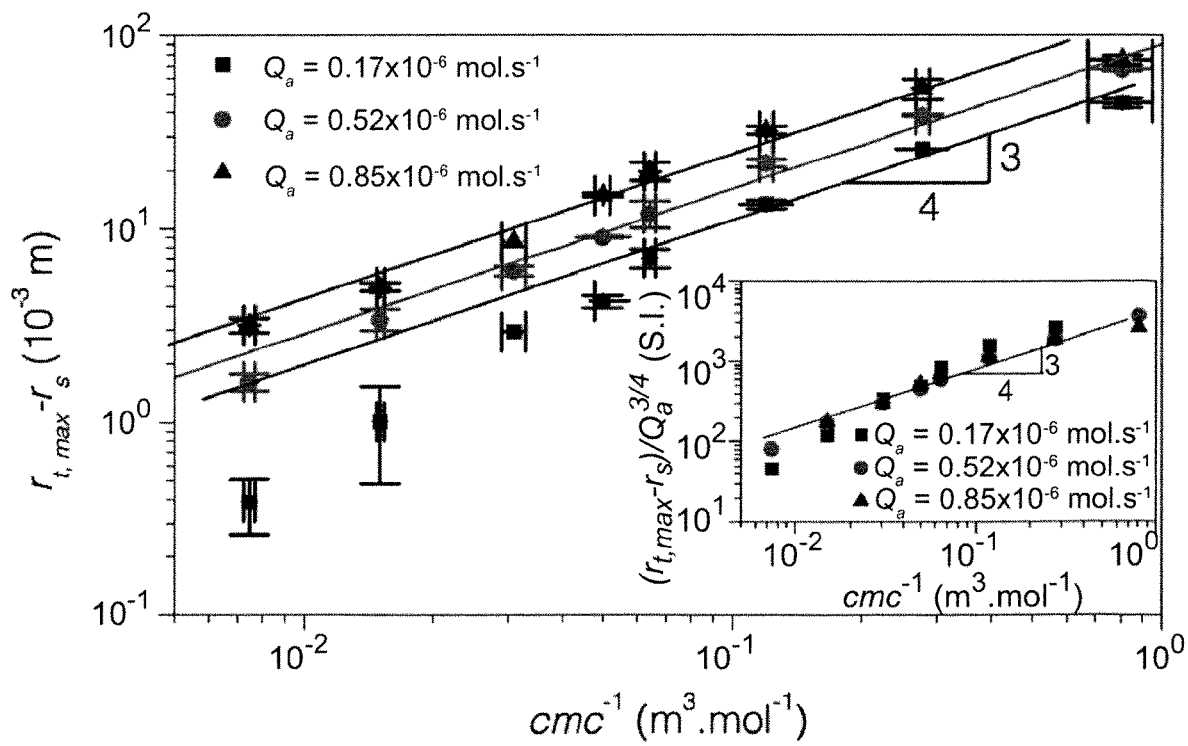

FIG. 4d is a graphic representation comparing the equation (7) and the experimental data for the maximal size of the transparent zone $r_{t,max}-r_s$ ($10^{-3}$ m) as a function of the inverse of the critical micellar concentration c* (inset: collapse of the experimental data for $r_{t,max}-r_s$ when values are rescaled by $Q_a^{3/4}$ as a function of cmc$^{-1}$; all points were measured for the same surfactant amount injected in the layer, $n_s=Q_a t=17.2×10^{-6}$ mol).

Figure 5A:

FIG. 5a is photographic top view of the top surface of the solvent layer, during injection of the traceable solution comprising olive oil (test done with a solution of SDoS ([SDoS]=0.26M), injected at a rate CL=0.28×10$^{-6}$ mol·s$^{-1}$).

Figure 5B:
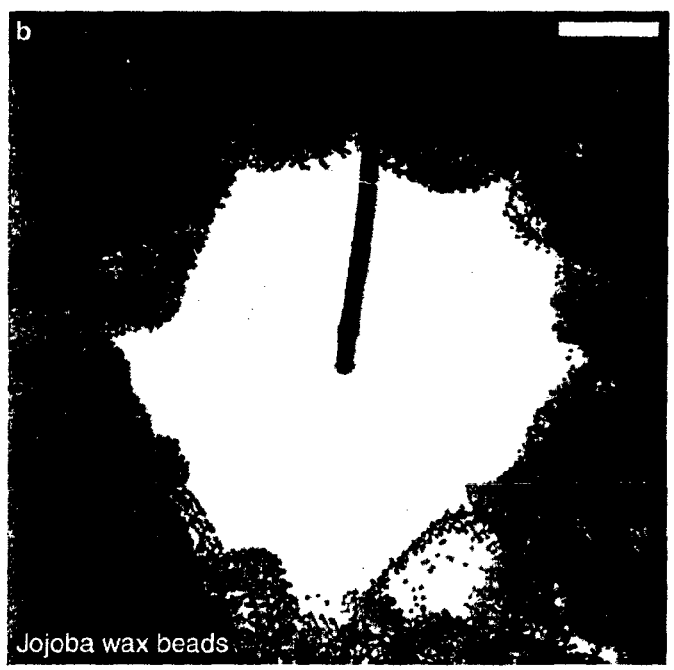

FIG. 5b is photographic top view of the top surface of the solvent layer, during injection of the traceable solution comprising jojoba wax particles (test done with a solution of SDoS ([SDS]=0.26M), injected at a rate $Q_a$=0.28×10$^{-6}$ mol·s$^{-1}$).

Figure 6A:
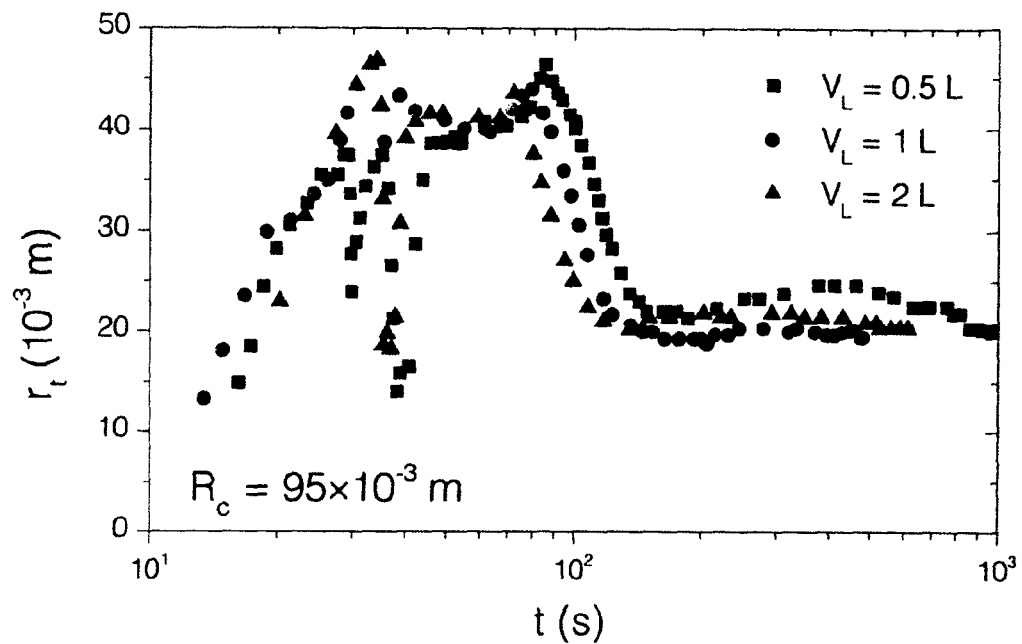

FIG. 6a is a graphic representation of the radius of the transparent zone $r_t$ as a function of t (s), for different volumes $V_L$ of solvent in the same container across experiments and identical molar flow rates $Q_a$.

Figure 6B:
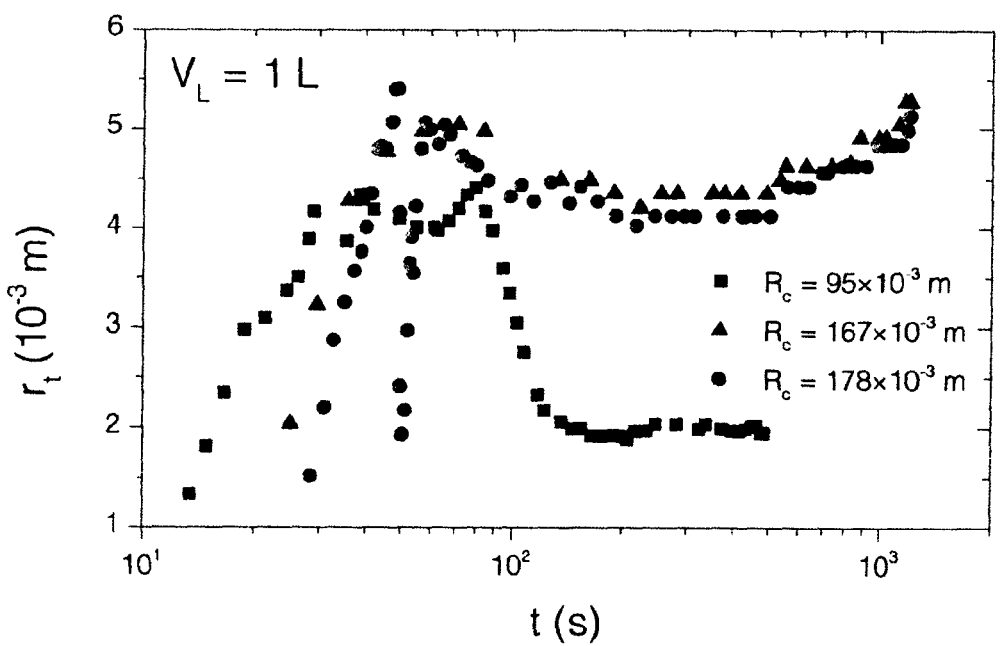

FIG. 6b is a graphic representation of the radius of the transparent zone $r_t$ as a function of t (s), for different size $R_c$ of the air/water interface at constant volume and flow rate.

Figure 7A:
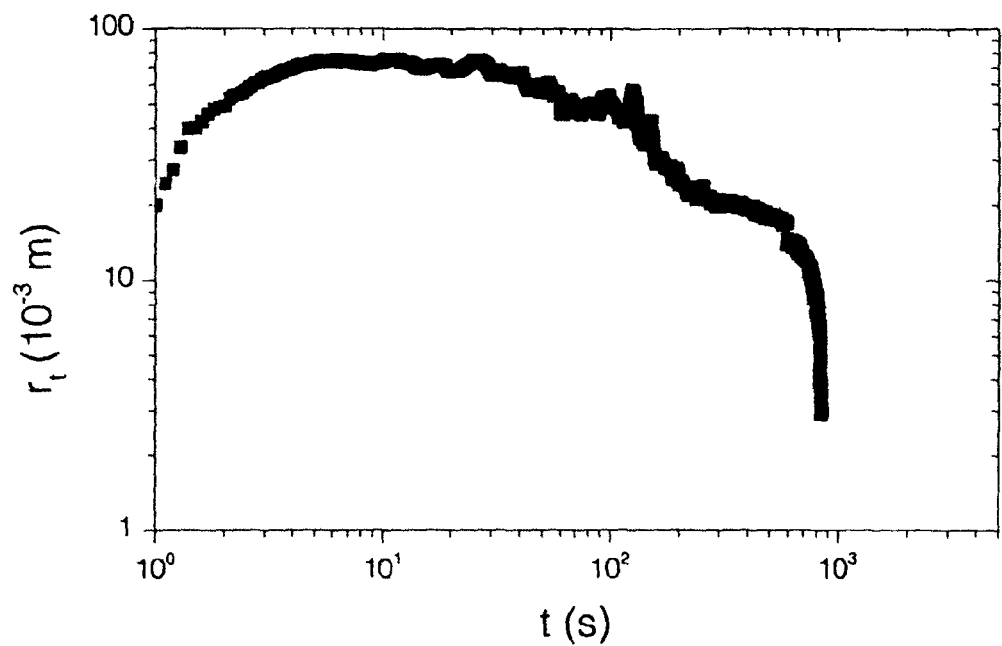

FIG. 7a is a graphic representation of the radius of the transparent zone $r_t$ as a function of t (s), for hexadecyltrimethylammonium chloride, $C_{16}$TAC.

Figure 7B:
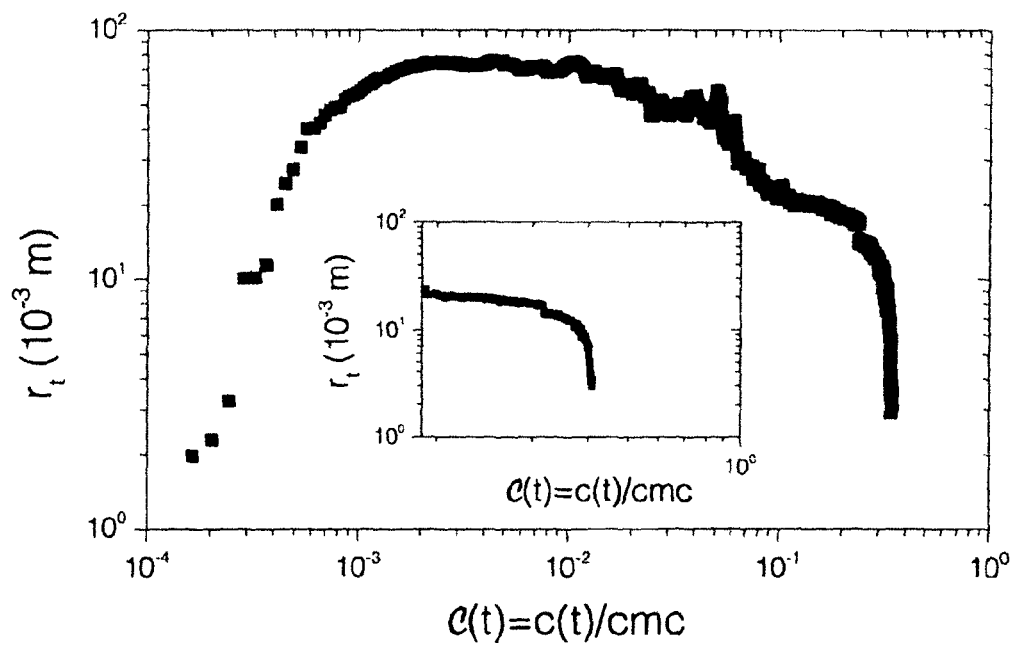

FIG. 7b is a graphic representation of the radius of the transparent zone $r_t$ as a function of C(t)=c(t)/cmc.

Figure 8:
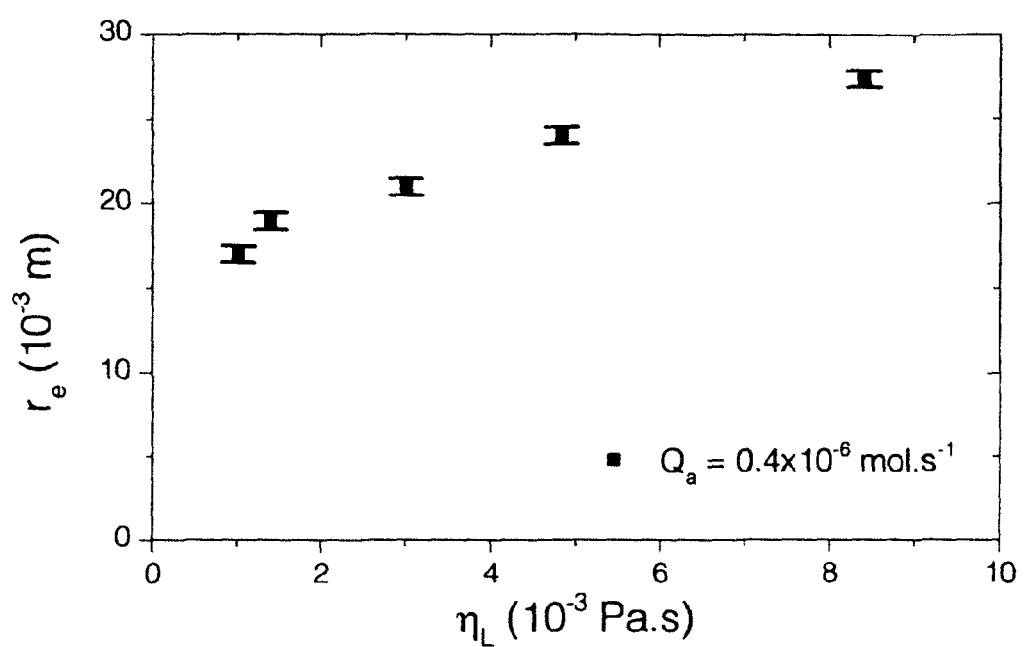

FIG. 8 is a graphic representation of the radius of the transparent zone $r_t$ as a function of the viscosity $\eta_L$ ($10^{-3}$ Pa·s).

SUMMARY OF THE INVENTION

As used herein, the term "amphiphile" or "amphiphilic compound" means molecules comprising both at least one hydrophobic part and at least one hydrophilic part. In bulk, water molecules interact through hydrogen bonds. The presence of a non-polar molecule such as a hydrocarbon distorts the bond network. The amplitude of the distortion dictates the miscibility of nonpolar compounds. This interaction is known as the hydrophobic effect. The substitution of one end-methyl-group hydrogen atom with a polar molecule confers both hydrophilicity and hydrophobicity to the compound, which is then amphiphilic. For the same hydrocarbon chain, the miscibility limit of the amphiphilic compound, i.e. the concentration before phase separation, will be orders of magnitude greater than the miscibility limit of the pure hydrocarbon. From a thermodynamic standpoint, the addition of amphiphilic compounds increases the free energy of a volume of water. To minimize free energy, amphiphilic compounds may either adsorb at the interface between water and another medium or form aggregates that encapsulate the hydrocarbon tails of the amphiphilic compounds, such as micelles. At low amphiphile concentrations, adsorption is more efficient at decreasing the total free energy. In this regime, the interfacial amphiphile concentration is at equilibrium with the bulk concentration. To be specific, these compounds can self-assemble when they are dispersed in water, and they form two- or three-dimensional aggregates such as monolayers, bilayers and micelles (see Israelachvili, J. N. Intermolecular and surface forces, $3^{rd}$ edn, Academic press, 2011), which can compartmentalize matter, as in lipid-covered cells and organelles, lipid vesicles and surfactant-stabilized dispersions like emulsions and foams.

As used herein, the term "Marangoni" or its equivalent term "Marangoni effect" means the mass transfer and induced-flow along an interface between two fluids due to the surface tension gradient. The presence of adsorbed amphiphiles affects the physical properties of a water-fluid interface, such as its interfacial tension. Heterogeneities in the surface amphiphile distribution induce a gradient of interfacial tension $\Delta y$, which in turns drives a flow directed from regions of low surface tensions to regions of high surface tensions. The Marangoni effect can be induced either by increasing rapidly the area of the surfactant-covered interface (Breward, C. J. W., Darton, R. C., Howell, P. D. & Ockendon, J. R. The effect of surfactants on expanding free surfaces. Chem. Eng. Sci. 56, 2867-2878, 2001; Howell, P. D. & Breward, C. J. W. Mathematical modeling of the overflowing cylinder experiment. J. Fluid Mech. 474, 275-298, 2003; Bain, C. D. The overflowing cylinder sixty years on. Adv. Colloid. Interfac. 144, 4-12, 2008) or by adding supplementary surfactants to the interface of a water-fluid system containing an initial arbitrary amount of amphiphiles.

As used herein, the term "critical micellar concentration" or "CMC" means the concentration of surfactants in bulk, above which micelles form and all additional surfactants added to the system go to micelles.

As used herein, the term "corona" means the second region flow i.e. the transparent zone. Both terms "corona" and "transparent zone" are used interchangeably in the present application.

Disclosed is a new process and device to measure important physicochemical parameters of chemicals such as lipids, soaps, surfactants, when they are diluted in a solvent. These chemicals are widely referred as to amphiphiles. Among these physical properties, the present invention allows measuring the critical micellar concentration (cmc) of amphiphiles with a single quick measurement, whereas existing techniques are time consuming and require one to measure the complete variation of one parameter (surface tension, . . . ) against another (amphiphiles concentration in water, . . . )

A straight forward use of the method and device thereof, according to the present invention, would be in the design of a new apparatus for lab equipment which would allow the reliable and fast characterization of an amphiphile, such as a soap, lipids, . . . . Another use is to adopt the disclosed procedure to measure physical properties that are reported as part of characterization of materials.

The present invention relies upon the phenomena known as the Marangoni flow. In 2D aggregates, a heterogenous distribution of amphiphilic compounds triggers an interfacial-tension-induced Marangoni flow (Levich, V. G. & Kryslov, V. S. Surface-tension-driven phenomena. Ann. Rev. Fluid Mech. 1, 293-316, 1969; Matar, O. K. & Craster, R. V. Dynamics of surfactant-assisted spreading. Soft Matter 5, 3801-3801, 2009), which is critical to the understanding of transport phenomena in lipid nanotubes, the formation of lipid tethers, the stability of emulsions and foams, pulmonary surfactant replacement therapy and many industrial applications. Particularly, the effect of the miscibility of amphiphiles with water has been scrutinized (Halpern, D. & Grotberg, J. B. Dynamics and transport of a localized soluble surfactant on a thin film. J. Fluid. Mech. 237, 1-11, 1992; Jensen, O. E. & Grotberg, J. B. The spreading of heat or soluble surfactant along a thin liquid flim. Phys. Fluids A 5, 58-68, 1993; Lee, K. S. & Starov, V. M. Spreading of surfactant solutions over thin aqueous layers: influence of solubility and micelles disintegration. J. Colloid Interface Sci. 314, 631-642, 2007; Lee, K. S. & Starov, V. M. Spreading of surfactant solutions over thin aqueous layers at low concentrations: Influence of solubility. J. Colloid Interface Sci. 329, 361-365, 2009).

In the present invention, the inventors have demonstrated that the degree of miscibility of amphiphilic compounds in a solvent, e.g. water, sets i.e. is correlated with the finite area across which a Marangoni flow is observed at the surface of the solvent, e.g. water, when the amphiphilic compounds are constantly supplied to the surface. The inventors have also demonstrated that the velocity field has universal features, and they have identified the scaling laws that capture both the size of the area in which the Marangoni flow is observed and the magnitude of the maximum velocity in this area. Hence, the inventors have demonstrated that such correlation and scaling can be leveraged in order to assess the solubility of amphiphilic compounds in a solvent, particularly for measuring specific physicochemical parameters of amphiphilic compounds, more particularly for measuring the critical micellar concentration of amphiphilic compounds. The demonstration and findings made by the inventors establish the basis for a new fast method to measure the critical micelle concentration of amphiphiles. Indeed, as explained hereinbefore, measuring the cmc often requires the time-consuming measurement of one property of a solution of amphiphiles such as its surface tension as a function of amphiphile concentration. In contrast, the present method provides an estimate of the cmc from a single measurement of the size of the spreading area at a given flow rate, accompanied by a single independent measure of the surface tension of the solution.

In a first aspect, the present invention relates to a method for assessing the solubility of amphiphilic compounds in a solvent, particularly to a method for measuring different physicochemical parameters of amphiphilic compounds, more particularly to a method for measuring the critical micellar concentration of amphiphilic compounds. The method according to the present invention comprises the steps of:

providing a solvent;
preparing a layer of solvent;

preparing and providing a solution comprising amphiphilic compounds;

dispersing tracing particles into the solution;

injecting the traceable solution at the surface of the solvent layer;

taking pictures of the surface of the solvent layer, upon injection of the traceable solution, and determining the radius r of the corona formed (as a function of the injected flow rate);

assessing the velocity u of the tracing particles dispersed into the traceable solution, upon injection of said solution to the surface of the solvent layer, and determining the maximum velocity $u_{max}$ of the tracing particles (again as a function of the injected flow rate); and from the radius of the corona and the amplitude of the velocity (and for various injection flow rates), determining the specific physicochemical properties of the amphiphilic compounds, preferably determining the critical micellar concentration of the amphiphilic compounds.

Employing the disclosed process and device, physicochemical parameters can be measured quickly and easily by performing a single large-scale measurement. Existing (equilibrium) techniques are usually time consuming: it can take a few days to measure physicochemical parameters such as diffusion constants or the critical micellar concentration, whereas the disclosed process delivers these pieces of information in a few minutes, by running a simple experiment based on spreading of the chemical at the interface between the solvent and air.

Steps of the disclosed process and device comprise:

preparation of a layer of solvent a few centimeters thick preparation of the solution of surfactant to be tested in the same solvent dispersion of tracing particles to follow the flow injection of the particle-seeded surfactant solution at a constant flow rate using a pump at the surface of the layer of solvent during injection, pictures of the surface of the layer are taken. This allows for the measurement of the so-called corona, whose size is one of the key parameters in the experiment at the same time, the velocity of the tracing particles need to be tracked either through high speed imaging or with other velocimetric techniques. From this measurement, the maximum velocity of the tracers must be extracted.

the velocity must be plotted against the radius, and from this measurement the physicochemical properties of the amphiphiles can be deduced.

Should the size over which the flow to be visualized extends become either too small for very soluble surfactants or too large for rather insoluble surfactants, this can be tuned by adjusting the injection flow rate or the size of the container.

Many chemicals are characterized by their solubility or affinity in a solvent. The disclosed process and device allow one rapidly assess this effect and to quantify it.

This method has been developed after studying how the affinity between the solvent, e.g. water, and the amphiphilic compounds affects Marangoni flows at the interface between air and the solvent, e.g. water such as ultra-pure water.

The present invention comprises the step of providing a solvent. Any suitable solvent may be used. In a specific embodiment, the solvent is water, preferably ultra-pure water. The solvent is substantially free of amphiphilic compounds such as surfactants.

The present invention comprises the step of preparing a layer of solvent. The solvent layer is preferably a few centimeters thick.

The layer may have a thickness h ranging from 1 cm to 10 cm, preferably from 2 cm to 4 cm, more preferably from around $10^{-2}$ m.

The present invention comprises the step of preparing and providing a solution comprising amphiphilic compounds, such as surfactants, and a suitable solvent. This solution is aimed at being tested in the same solvent.

The amphiphilic compounds may be selected from the group consisting of lipids, soaps, surfactants, and mixtures thereof. The solvent may be an aqueous solvent, preferably water.

In a preferred embodiment, the solution is an aqueous solution of hydro-soluble surfactants.

The solution comprises a concentration c of amphiphilic compounds such as c is preferably 5 to 15 times the cmc (10 times the cmc is optimal). But all concentration above the cmc can be used.

The present invention comprises the step of dispersing tracing particles. The tracing particles are dispersed into the solution, in order to obtain a traceable solution. As used herein, the term "traceable solution" means that the solution comprises amphiphilic compounds and tracing particles into a suitable solvent. When the amphiphilic compounds are surfactants, the solution is a called surfactant solution and the traceable solution is called a traceable surfactant solution. Such dispersion allows following the flow.

The tracing particles must be initially dispersed into the surfactant solution, and the dispersion must be stable over the experimental time (tens of minutes). The tracers may be selected from the group consisting of oils, clean oil like dodecane can be used, but commercial olive oil are also suitable. If oil is used, the surfactant solution containing the dispersed oil droplets is an emulsion. It can be prepared by any type of emulsifier; and the remaining size of the droplets is about 10 microns. Solid particles may also be suitable tracers.

The traceable solution may comprise from 30% to 60%, preferably from 40% to 50% of tracing particles when compared to the total volume of the total solution.

Indeed, both ultra-pure water and surfactant solutions are transparent. In order to follow the flow of the solution, there is the need therefore for incorporating a tracing particle. Indeed, the flow of the solution may be visualized for example with the droplets formed by dispersing oil in the surfactant solution prior to the experiments at a ratio $\theta = V_a/(V_a+V_0)$ with $V_a$ and $V_0$ being the volumes of surfactant solution and oil respectively. The inventors have found that identical results were obtained with different kind of particles and different oils. As a result, tracing particles added the solution act as passive tracing particles. Therefore, the total flow rate Q was replaced by the surfactant flow rate $Q_a$ (mol/s)=Q·θ·c presently.

The present invention comprises the step of injecting the traceable solution at the surface of the solvent layer. The injection is preferably performed at a total constant flow rate Q. The traceable solution may be injected at the surface of the solvent layer using a pump means. To be specific, this step allows bringing the traceable solution, such as an aqueous solution of hydro-soluble surfactants, at a constant flow rate to the free surface of a deep layer of solvent initially substantially free of amphiphilic compounds, such as initially surfactant-free pure water.

The total flow rate Q may range from 0.5 mL/min to 20 mL/min, preferably from 1 mL/min to 10 mL/min (when the surfactant solution is 10 times the cmc). It is preferable to define the flow rate in terms of number of molecules/s: the typical range is 1 to 10 micromole/s.

The present invention comprises the step of taking pictures of the surface of the solvent layer. This step is preferably concomitant to the step of injecting the traceable surfactant solution to the surface of said solvent layer. This step allows measuring the so-called corona, particularly the radius r of the corona. The size of the corona is one of the key parameters in the experiment.

The present invention comprises the step of assessing the velocity u of the amphiphile compounds. The velocity u of the amphiphile compounds is assessed indirectly by assessing the velocity u of the tracing particles dispersed into the surfactant solution. Such assessment may be performed using high-speed imaging devices or any other suitable velometric techniques. This step is preferably concomitant to the step of injecting the traceable surfactant solution to the surface of said solvent layer. This step allows determining the maximum velocity $u_{max}$ of the tracing particles, hence the maximum velocity $u_{max}$ of the amphiphile compounds.

The present invention further comprises, from these measurements, determining the specific physicochemical properties of the amphiphilic compounds tested, particularly determining their critical micellar concentration.

In a preferred embodiment, the present invention further comprises the step of measuring the surface tension $\gamma_s$ of the solution, particularly measuring the gradient $\Delta\gamma$ of surface tension between the solvent layer and the traceable solution. The inventors have demonstrated indeed that the method according to the present invention provides an estimate of the cmc from a single measurement of the size of the spreading area at a given flow rate, accompanied by a single independent measure of the surface tension of the solution.

In a second aspect, the present invention relates to a device for assessing the critical micellar concentration of amphiphilic compounds comprising:
  a container, for storing the traceable solution comprising amphiphilic compounds;
  a tank, for containing the solvent layer;
  an injection means, connected to the storage container, and located over the tank, wherein the injection means is suitable for injecting the traceable solution at the surface of the solvent layer;
  a pumping means, for assisting the injection of the traceable solution at the surface of the solvent layer;
  an image-recording apparatus, for recording and/or taking pictures of the surface of the solvent layer, upon injection of the traceable solution; an image-processing apparatus, for processing the images and/or movies obtained with the image-recording apparatus;
  a computer for measuring the physicochemical parameters of the amphiphilic compounds.

DETAILED DESCRIPTION OF THE INVENTION

In order to achieve the present invention, the inventors have conducted a series of experiments, as reported in the Example Section hereinafter. Particularly, the following identification, characterization, demonstration, and analysis, were carried out:
  Characterization of the Marangoni flow Identification of the flow regions by light scattering, and analysis of the profile and the magnitude of the velocity field;
  Analysis of the profile and the magnitude of the velocity field of the flow regions;
  Characterization of the transparent zone Analysis of the dependence of the flow regions;
  Characterization of the transparent zone Determination of the dependence between the radius of the transparent zone and the injection flow rate $Q_a$;
  Characterization of the velocity field;
  Demonstration of the universality of the velocity field in the transparent zone, determination of the scaling laws and validation of the scaling laws;
  In addition, the following studies, as a support of the previous experiments, were conducted:
  Passiveness of the tracers;
  Influence of tracer packing on the radius of the transparent zone;
  Radius of the transparent zone as a function of time and concentration
  Measurement of the velocity field
  Influence of viscosity on the radius of the transparent zone As shown on FIGS. 1b and 1c, it is shown a typical interfacial flow pattern, wherein three flow regions are discriminated using the intensity of light scattered by the tracing particles. It is identified a first region as the source, with radius $r_s$; a second region as the transparent zone, of radius $r_e$, and which surrounds the source. No scattered light is visible in the transparent region, suggesting that the surface density of tracers is very low. Outside the transparent zone, a region of strong light scattering is observed, and vortical structures grow and expand outwardly. Further from the source, the droplets are moving only slightly, suggesting that surface tension is spatially homogenous in this region and that the Marangoni flow is located in the transparent zone. As shown in FIG. 1b, it is also revealed the existence of a bulk flow that originates from the edge of the transparent zone, with its direction opposing the interfacial flow. To be specific, it is revealed the existence of a three-dimensional recirculating flow in the bulk fluid below the transparent zone, which changes direction at $r=r_t$ and then follows the bottom of the container back towards the source. The slow interfacial vortices might be related to the fate of surfactants at the air/water interface in the outer region, which does not have a significant influence on the main flow characteristics relevant to the transparent zone, as show hereinafter.

As shown on FIG. 1d, the three regions also differ by the profile and the magnitude of the velocity field. In the source, the velocity is approximately constant and on the order of several $10^{-2}$ m·s$^{-1}$. Then the particles accelerate until they reach a maximum velocity $u_{max}$), on the order of 0.5 m·s$^{-1}$ and then decelerate as particles travel across the transparent area. The particles decelerate rapidly when they reach the boundary between the transparent zone and the outer region.

As shown in FIG. 2a, the extent of the different flow regions depends on both the chemical structure of the amphiphiles and the flow parameters. For a constant total flow rate Q and ratio θ, the radius of the transparent zone $r_e$ increases as the number of carbon atoms $N_c$ in the hydrocarbon chain of the amphiphiles increases. As reported in FIG. 2b, a systematic study of $r_e$ as a function of $N_c$ shows that $r_e$ varies over almost 2 orders of magnitude when the length of the carbon chain increases twofold.

Moreover, the nature of the polar group matters. For example, for identical times in the experiment, the radii obtained for SDS ($N_c$=12) and DoTAB ($N_c$=12) are different by almost a factor of 2. Indeed, $r_t$ is sensitive to the properties of the surfactant polar headgroup, in particular to its effective radius $r_{eff}$ during micellization, which depends on the affinity of the co-ion and the counterion with water.

For example, an increase of $r_{eff}$ by using $C_{12}NASO_4$ instead of $C_{12}TAB$, which differ only by their polar headgroups, results in a decrease of $r_t$.

Finally, $r_e$ also varies with time. The observed decrease is related likely to the increase of the surfactant concentration in the initially clean layer of ultra-pure water. Nonetheless, an analysis along these lines indicates that concentration variations are not sufficient to explain the temporal evolution of $r_e$. After an initial increase at the onset of injection, $r_t$ remains constant at a maximal value $r_{t,max}$ for a time dependent on finite-size effects due to the container. Then, $r_t$ decreases slowly, before a sharp decrease is observed at longer times, corresponding to a significant increase of the surfactant concentration in the water layer.

As shown in FIG. 2c, the radius of the transparent zone $r_{t,max}$ also increases non-linearly with an increase of the injection flow rate $Q_a$. The contour of the transparent zone remained stable for all of the flow rates we worked at. The size of the source $r_s$, equal to the diameter of the needle at small flow rates, increases above a threshold flow rate, which seems constant whatever the formulation of the injected solution.

To gain a better understanding of the mechanisms setting the properties of the Marangoni flow observed, the relation between the velocity profiles in the transparent zone and the experimental conditions was investigated. The complete velocity field was measured at once for a range of $r_e$; both the particles and the transparent zone in its entirety could not be seen for surfactants with $N_c$ of 14 or more. As shown in FIG. 3a, the tracers moved along the radial direction only with a velocity u, and the velocity keeps qualitatively the same shape for all of the surfactants tested. As for the size of the transparent zone, the length of the carbon tail of the surfactants and the nature of the polar group influence the properties of the velocity field drastically. In particular, lengthening the hydrophobic tail of the surfactants leads to a decrease of the magnitude of the maximum velocity $u_{max}$ of the flow. A comparison of the velocity fields obtained for SDS and DoTAB shows that the nature of the polar head influences also the value of $u_{max}$), for similar carbon tails. The injection flow rate has little to no effect on the typical magnitude of the velocity field.

Guided by the similarity of the velocity profiles obtained for surfactants with very different affinities with water (see FIG. 3a), it was investigated their universality, in particular in the transparent zone. To do so, the location of the boundary of the source $r_s$ was set as the origin of radial coordinates. These coordinates are then rescaled by the size of the transparent zone $r_e - r_s$ and become $R = (r - r_s)/(r_e - r_s)$, while velocities are simply rescaled as $U = u/u_{max}$. As shown in FIG. 4a, this rescaling is able to collapse quite well the radial velocity fields obtained from different surfactants on a master profile. The location at which U=1 is located around R=0.2. The profiles display a very similar shape during the deceleration stage following the reach of U=1. A distinction depending on the surfactant used for the experiment appears in the vicinity of the boundary between the transparent zone and the outer dense region. Without wishing to be bound by any theory, it is believed that this difference may be related to the details of the force balance at play in this region.

The universality of the velocity fields suggests that a theoretical analysis of the spreading of hydrosoluble surfactants on water in terms of scaling arguments, combining the hydrodynamics of the bulk layer and surfactant physico-chemical properties, may capture the features of the flow in the transparent zone. The bulk and the interface of the layer are initially quiescent and surfactant-free. After we begin injecting surfactants, the Marangoni stress induced by the difference between the surface tension of the injected solution and that of ultra-pure water far from the source triggers a flow close to the interface, and momentum diffuses towards the bulk of the layer. In steady case, the balance between the convection and diffusion results in a viscous boundary layer with thickness:

$$-I_v \approx \sqrt{(\nu r^*)/u^*)}, \quad \text{Equation (1)}$$

with $v = \eta/\rho$, $\eta$ and $\rho$ respectively the dynamic viscosity and the density of the fluid in the layer, $u^*$ a characteristic velocity at the interface and $r^*$ the distance over which radial velocity gradients are established, i.e. the size of the flow to be determined. It is assumed that surface tension gradients in regions extending to $r > r^*$ are much smaller than in the area defined by $r < r^*$.

The fluid moving along the interface advects surfactants. As there is no surfactant far from the interface, surfactants desorb and diffuse towards the bulk. It is assumed that adsorption/desorption processes occur on timescales much shorter than the surfactant diffusion in bulk water. Interface-bulk mass exchange is thus diffusion-limited, and a mass transfer boundary layer grows, whose thickness scales as:

$$-I_c \approx \sqrt{((Dr^*)/u^*)} = Sc^{-1/2} I_v, \quad \text{Equation (2)}$$

with $Sc = (v/D)$ the Schmidt number, which compares the kinematic viscosity v, i.e. momentum diffusion constant, to the surfactant bulk diffusion constant D. Equation (2) is valid if the viscous boundary layer is much larger than the mass transfer boundary layer, i.e. if $Sc \gg 1$, a condition that is fulfilled in our case as, for a diffusion coefficient $D = 10^{-10}$ $m^2 \cdot s^{-1}$ and $v = 10^{-6}$ $m^2 \cdot s^{-1}$ for water, $Sc \approx z 10^4$. The bulk concentration thus varies from a high value just below the interface to zero at the bottom of the mass boundary layer. The cmc of the surfactants is chosen as the concentration scale relevant to the description of surfactant transport because of the dependence of the radius of the Marangoni flow on the properties of both the hydrophobic tail and the polar headgroup of the surfactants, which are key elements in the thermodynamic definition of the cmc.

The rationale is based on the assumption that the Marangoni flow stops when surfactants injected at the source at a molar flow rate $Q_a$ have all desorbed from the interface. Hence the surfactant mass balance can be expressed as:

$$-Q_a \propto r^{*2} \cdot D \cdot (c^*/I_c), \quad \text{Equation (3)}$$

with $c^*$ the critical micelle concentration.

Replacing $I_c$ by Equation (2), it is found:

$$-Q_a \propto r^{*3/2} \cdot (Du^*)^{1/2} \cdot c^*, \quad \text{Equation (4)}$$

From the continuity of stress at the interface:

$$-(\eta u^*)/I_v \approx (\gamma_w - \gamma_s)/r^*, \quad \text{Equation (5)}$$

with $\gamma_w$ the surface tension of ultra-pure water and $\gamma_s$ the surface tension of the surfactant solution. From the stress boundary conditions, we obtain an expression for the velocity $u^*$:

$$-u^* \propto A[(\gamma_w - \gamma_s)^2/(\eta \rho r)]^{1/3}, \quad \text{Equation (6)}$$

And by replacing $u^*$ in Equation (4) with Equation 6, it is obtained:

$$-r^* \propto B[(\eta \rho)/(\gamma_w - \gamma_s)^2 D^3]^{1/8} \cdot (Q_a/c^*)^{3/4}, \quad \text{Equation (7)}$$

where A and B are two dimensionless prefactors. In a preferred embodiment, prefactor A=1 and prefactor B=1.

It is estimated that the values predicted for $u^*$ and $r^*$ with typical values of the different parameters involved in equations (6) and (7) while assuming that $(\gamma_w-\gamma_s)$ is constant for all experiments and equal to 33 mN·m⁻¹, a realistic value for the surfactant solutions we used. Setting both A and B to unity, we find $u^* \approx 0.5$ m·s⁻¹ and $r^* \approx 15 \times 10^{-3}$ m, which compare very well with the experimental findings for the maximum velocity, as reported in FIG. 3.

Equation (6) is compared to the experimental data by taking $u^*=u_{max}$ and $r^*=r_{t,max}-r_e$. As shown in FIG. 4b, Equation (6) captures the experimental measurements very well, with a prefactor $A \approx 1$. This agreement supports our assumption of a constant interfacial tension difference ($\gamma_w-\gamma_s$). It is noted that equation (6) fails to capture the data for surfactants forming transparent zones comparable in size to the millimeter-long meniscus connecting the needle tip to water surface, which is not surprising since there is no length scale separation in this case.

The ¾ exponent of the power law in equation (7) is in excellent agreement with the experimental data for $(r_{t,max}-r_e)$ as a function of both $Q_a$ and $c^*$ (FIGS. 4c and 4d). The prefactor B in equation (7) is close to unity.

Equation (7) is also able to collapse the experimental data as a function of the cmc onto a master curve (inset in FIG. 4d). The discrepancy between equation (7) and data at high flow rates in FIG. 4c is related to the destabilization of the source. Preliminary experiments indicate that the disagreement between data and equation (7) at the lowest flow rate in FIG. 4d results from a decrease of the magnitude of $(\gamma_w-\gamma_s)$. Our experiments confirm that the radius $r_t$ of the transparent zone flow increases with an increase of the viscosity of the layer. Thus, the test of the scaling laws against the flow rate $Q_a$, the critical micelle concentration of the surfactants and the viscosity of the bulk layer show that equations (6) and (7) contain the appropriate physicochemical ingredients to describe Marangoni flows induced by water-soluble surfactants on water. Moreover, comparison between the scaling laws and the experimental data shows that the values of the prefactors in equations (6) and (7) are close to unity, thus providing further support to the validity of the theoretical arguments. Finally, as all the surfactants we used have similar bulk diffusion coefficients D, the results herein establish thereof the equilibrium cmc as a critical quantity to understand the out-of-equilibrium Marangoni flow.

Both scaling laws referred hereinbefore as equations (6) and (7) can also be expressed as follows:

$$-u=[\Pi^2/(\eta\rho r)]^{1/3} \quad \quad \text{Equation (6a)}$$

$$-r=[(\eta\rho)/\Pi^2]^{1/8} \times [Q/(D^{1/2}c^*)]^{3/4} \quad \quad \text{Equation (7a)}$$

with u being the velocity of the transparent zone, $\Pi$ being the surface pressure (i.e. the difference between the air/water interfacial tensions at the source and far from the source), q and p being the viscosity and the density of the liquid respectively, r being the size of the transparent zone, Q, being the flow rate, D being the bulk diffusion constant of the surfactant and $c^*$ being the solubility limit of the surfactant monomers, also known as the critical micellar concentration (cmc).

Such alternative expressions of the scaling laws lead to the same observations, demonstrations, and/or conclusion.

The first scaling law relating to the velocity u to r can be easily tested as most of its parameters are well known experimentally except for the surface pressure $\Pi$. To check the validity of equation 6(6a), it was identified u with $u_{max}$ and r with $r_e-r_s$. It was taken $\eta=10^{-3}$ Pa·s, $\eta=10^3$ kg·m⁻³, and it was chosen $\Pi=35$ mN·m⁻¹, as a realistic value of surface pressure for all of the surfactants used in the present application. As shown in FIG. 4b, equation 6(6a) captures the experimental measurements very well for most of the surfactants used. A discrepancy is seen for surfactants forming small transparent zones. For these surfactants, the size of the transparent zone is comparable to the size of the meniscus connecting the tip of the needle to the surface of the water layer. Hence, it is likely that the maximal velocity is reached while the tracers are still travelling in the meniscus. Therefore we may measure a projection of the velocity on the surface of the water layer that is smaller than the actual velocity.

It was identified Q with $Q_a$ and $c^*$ with the solubility limit of the surfactant monomers, also known as the critical micellar concentration (cmc). It was mostly focused on the dependence of $r_e-r_s$ on $Q_a$ and the cmc of the surfactants, checking if the scalings $r_e-r_s \propto Q^{3/4}$ and $r_e-r_s \propto cmc^{-3/4}$ were valid. As shown in FIGS. 4c and 4d, the equation 7(7a) captures very well the experimental trends over large ranges of both the flow rate (see FIG. 4c) and the cmc (see FIG. 4d). Experimental data deviate from $r_e-r_s \propto Q_a^{3/4}$ at high flow rates and seem to saturate. This saturation is difficult to test though as the stability of the source decreases with further increases of Q. The threshold flow rate at which the deviation occurs depends on the surfactant. As shown in FIG. 4d, the scaling law $r_e-r_s \propto cmc^{-3/4}$ describes very well the experimental data for the two highest flow rates $Q_a=0.52 \times 10^{-6}$ mol·s⁻¹ and $Q_a=0.85 \times 10^{-6}$ mol·s⁻¹, with a discrepancy between experiments and theory at high flow rates, in agreement with FIG. 4c. In contrast, equation 2 captures experimental data only over a small range of cmc's at the lowest flow rate $Q_a=0.17 \times 10^{-6}$ mol·s⁻¹.

EXAMPLE

Materials

The experiments were performed with eight different surfactants. All surfactants were used above their Krafft point, i.e. their cmc is well defined. The cmc of these surfactants varies over almost two orders of magnitude. These molecules were used because they have similar molecular weights, and the interfacial tension of their aqueous solutions at concentrations above the critical micelle concentration is very similar, between 37 and 42 mN·m⁻¹. To avoid ageing effects, it was purchased surfactants before each experimental session and the surfactant solutions were prepared right before carrying out experiments. The surfactant concentration was 0.26M for all of the surfactant solutions except when mentioned otherwise, so that the surfactant concentration remained greater than the cmc of sodium octyl sulphate.

Oil droplets were formed prior to the experiments by dispersing a volume $V_o$ of oil in a volume $V_a$ of surfactant solution using turbulent mixing in a short pipe made of Tygon tubing (Saint Gobain, inner diameter $1.6 \times 10^{-3}$ m) connecting two 10-cc plastic syringes (Becton D Plastic). The droplets are polydisperse, with an average size of approximately 10 μm. Olive oil, silicone oil, safflower oil and canola oil were used to form the tracers. Changing the oil did not affect the flow, and it was checked that the surfactants carried by the droplets did not affect the flow.

The surfactant flow rate $Q_a$ was computed by multiplying the total emulsion flow rate Q by the volume fraction of surfactant solution $\theta=V_a/(V_a+V_o)$ and the concentration c of surfactants in the amphiphile solution, to give $Q_a=Q \cdot \theta \cdot c$. Experiments were performed in a square tank of side L=0.26 m. for every experiment, a volume of ultra-pure water (Millipore Q, resistivity σ=18.2 MΩ.cm) $V_L$=0.98 L to form the layer. The layer had a thickness $I=(14.5+/-1)\times10^{-3}$ m.

Methods

The surfactant solutions were injected using a syringe pump (Harvard Apparatus PHD 2000) at constant flow rates 0.036 mL·min$^{-1}$<Q<0.750 mL·min$^{-1}$ through a steel needle of outer diameter $d_o$=1.8×10$^{-3}$ m (Vita needle, Gauge 15). Becton D plastic syringes were used and connected to the needle using Tygon tubing (Saint Gobain, inner diameter $d_i$=1.59×10$^{-3}$ m). It was checked that the silicon piston did not affect the flow observed by performing experiments both with and without it. Movies were recorded using a vision Research Phantom v7.3 at frame rates 10<F<20 000 frames per second. The radius of the different regions of the flow was measured from spatio-temporal diagrams extracted from the movies using the reslice function in a custom version of ImageJ, FiJi. The diagrams were thresholded and then processed using custom MatLab code.

To measure the velocity fields, the position of the oil droplets was extracted from the movies using FiJi. The velocity fields were then computed by fitting the trajectory of the droplets with splines that were estimated to have the best compromise between roughness and fitting error. Because it was needed to see both the droplets and the entire transparent, velocity field measurements were only possible for surfactants with fewer than 14 carbon atoms in their carbon tail.

Characterization of the Marangoni Flow—Identification of the Flow Regions by Light Scattering, and Analysis of the Profile and the Magnitude of the Velocity Field As shown in FIG. 1a, the Marangoni flow of water induced by hydrosoluble surfactants was studied using eight surfactants from the alkyl trimethylammonium halides ($C_n$TABr, n=10 to 14; $C_n$TACl, n=12 and 16) as well as from the sodium alkyl sulfate ($C_n$NaSO$_4$, n=8 to 12) families (purchased from Sigma-Alrich before experimental run, purity 99%), whose critical micelle concentration varies over two orders of magnitude. Surfactant solutions, seeded with light-scattering 10-µm olive oil droplets, were supplied on the surface of a ultra-pure water layer millipore Q, resistivity σ=18.2 MΩ·cm) using a syringe pump (Harvard Apparatus PHD2000) at a constant surfactant molar flow rate $Q_a$=Q·θ·c, with θ=$V_s$/($V_s$+$V_{oil}$) the volume fraction of surfactant solution in the injected liquid, $V_s$ and $V_{oil}$ the volumes of surfactant solution and oil used to prepare the injected solution, Q the total volume flow rate and c the surfactant concentration.

As shown in FIG. 1b (scale bar 30×10$^{-3}$ m), a steel needle brings a solution of SDS ([SDS]=260×10$^{-3}$ M) seeded with olive oil droplets at the constant flow $Q_a$=0.52×10$^{-6}$ mol·s$^{-1}$. The solution forms a source of radius r, around the region of contact between the tip of the needle and the surface of the layer of pure water. A region with low light scattering intensity separates the source from an outer region where the intensity rises once again. The outer region is characterized by the presence of multiple vertical structures. The vortical structures that grow far from the source can be seen particularly on FIG. 1c (scale bar 30×10$^{-3}$ m).

Analysis of the Profile and the Magnitude of the Velocity Field of the Flow Regions As shown in FIG. 1d, the three regions across the air-water interface differ from each other by the magnitude of the velocities. Inside the source (r<$r_s$), the velocity increases from a few 10$^{-3}$ m·s$^{-1}$ to approximately 100×10$^{-3}$ m·s$^{-1}$. The velocity then increases slowly until the droplets enter the dilute zone where they experience a five- to tenfold increase of their velocities. The velocity then decreases slowly and dips sharply at the location corresponding to the boundary between the droplet-poor area and the outer droplet-rich zone. Although single objects become difficult to track outside the dilute area, tracking vortical structures shows that velocities in the dense region decrease from 5.10$^{-3}$ m·s$^{-1}$ close to the poor-dense boundary to approximately 0 far from the source.

Characterization of the Transparent Zone—Analysis of the Dependence of the Flow Regions Vis-à-Vis the Chemical Structure of the Amphiphiles and the Flow Parameters As shown in FIG. 2a (scale bar: 2×10$^{-2}$), the size of the transparent zone increases as the length of the carbon tail of the surfactant increases. Three surfactants were used from the $C_n$TAB family, with $N_c$=10, 12 and 14 carbons. $O_a$=0.52×10$^{-6}$ mol·s$^{-1}$. As illustrated by FIG. 2b, a systematic measure of the radius of the transparent zone $r_e$ as a function of time t for different surfactants shows that $r_e$ varies over almost 2 orders of magnitude when $N_c$ varies from 8 to 16. Data collected for HTAC (black square), ΠAB (clear square), SDS (black circle), DoTAB (clear circle), DoTAC (clear triangle), SDeS (clear lozenge), DeTAB (clear hexahedra) and SOS (clear right triangle). A comparison between the radius $r_e$ obtained for SDS and DoTAB shows that $r_e$ is also dependent on the nature of the polar head of the surfactant. $Q_a$=0.52×10$^{-6}$ mol·s$^{-1}$, c=260×10$^{-3}$ M.

Characterization of the Transparent Zone—Determination of the Dependence Between the Radius of the Transparent Zone and the Injection Flow Rate $Q_a$ As shown in FIG. 2c, the radius $r_e$ increases with an increase of the surfactant flow rate Q. The radius of the source $r_s$ increases above a threshold flow rate. Data collected for SDS with θ=0.4 and [SDS]=260×10$^{-3}$ M.

Characterization of the Velocity Field

As shown in FIG. 3a, at constant flow rate, the magnitude of the velocity in the transparent zone is function of the chemical structure of the surfactant. Data collected SDeS (black square), DoTAB (clear triangle) and SDS (grey circle).

In FIG. 3b, it is shown the velocity for SDeS at different flow rate. When the tracers leave the source, where u≈=10$^{-2}$ m·s$^{-1}$, they accelerate, reach a maximum velocity $u_{max}$≈0.5 m·s$^{-1}$, before decelerating as they travel across the transparent area. Finally, tracers decelerate abruptly as they reach r=$r_t$. The magnitude of $u_{max}$, decreases with an increase of n and/or $r_{eff}$.

Demonstration of the Universality of the Velocity Field in the Transparent Zone and Determination of the Scaling Laws FIG. 4a demonstrates that a rescaling of the velocity profiles by the maximal magnitude of the velocity U=u/$u_{max}$ and the position of the boundaries of the source of the transparent zone R=(r-$r_s$)/($r_e$-$r_s$) shows that these profiles are quasi-universal. The profiles differ mostly by the last decelerating stage observed close to the boundary between the transparent zone and the outer dense region. Data collected for SDS (clear square), DoTAB (clear triangle), DoTAC (clear circle) and SDeS (clear lozenge). $Q_a$=0.51× 10$^{-6}$ mol·s$^{-1}$, c=260×10$^{×3}$M.

As reported in FIG. 4b, the scaling law relating $u_{max}$ to the size of the transparent zone $r_e$-$r_s$ was tested. Continuous line: $\mu=[\Pi^2/(\eta\rho(r_e-r_s))]^{1/3}$, with $\Pi$=35×10$^{-3}$N·m$^1$, $\eta_{10}^{-3}$ Pa·s and η=10$^3$ kg·m$^{-3}$. Inset: log-log representation of the data.

As reported in FIG. 4c, the scaling law relating the maximal size of the transparent zone $r_e$-$r_s$ to the surfactant flow rate was tested $Q_a$. Data collected for SDeS (black circle), SDS (grey triangle), HTAC (black square). Continuous line: $r_{e,max}-r_s \propto Q_a^{3/4}$.

As reported in FIG. 4d, the scaling law relating to the maximal size of the transparent zone $r_{e,max}-r_s$ to the inverse of the critical micellar concentration (cmc$^{-1}$) of the surfactants was tested. Inset: comparison between the scaling law $r_{e,max}-r_s \propto$ cmc$^{-3/4}$. (continuous line) and experimental observations. Data collected for $Q_a$=0.17×10$^{-6}$ mol·s$^{-1}$ (black square), $Q_a$=0.51×10$^{-6}$ mol·s$^{-1}$ (grey circle), $Q_a$=0.85×10$^{-6}$ mol·s$^{-1}$ (black triangle).

In support of the experiments reported hereinbefore, the following experiments and/or observations were carried out:

Passiveness of the Tracers

In FIG. 5a and FIG. 5b, it is shown a comparison between the flow visualized with emulsions formed of 1/3 solutions (sodium dodecyl sulphate (SDoS), [SdoS]=260×10$^{-3}$M) and ⅔ olive oil similar to the solutions used in the experiments described herein, and the flow obtained by injecting a solution containing surfactants only and visualized using manually seeded jojoba wax beads (diameter 2×10$^5$ m<D$_J$ 6×10$^{-5}$ m, density d≈900 kg. m$^{-3}$) shows that the extent of the transparent area does not depend on the kind of tracers used. The white circle on FIG. 5b denotes the size of the transparent zone measured on FIG. 5a, which corresponds to the location where the vertical structures start to expand. As one can see, the circle in FIG. 51b remains particle-free indicating that the size of the transparent zone is not influenced by the nature of the tracers. The surfactant flow rate is the same for both systems, $Q_a$=0.28×10$^{-6}$ mol·s$^{-1}$, and pictures are taken at the same time after injection, t=33 s. The structure of the flow is obtained in a single shot using the emulsion, while 20 pictures had to be summed to obtain the same information from the experiments with jojoba particles.

The Influence of Tracer Packing on the Radius of the Transparent Zone

The radius $r_t$ of the transparent zone is a function of time. In the experiments described herein, it is noticed that $r_t$ decreased after a time on the order of 100 s. Although this decrease could be attributed to an increase of the concentration of surfactants in the layer of water, a calculation shows that the surfactant concentration at the time of decrease is too small (c=10$^{-2}$ cmc for C$_{16}$TAC, the surfactant with the lowest cmc) to induce a change of interfacial tension significant enough to modify the magnitude of the Marangoni stress. The decrease of the radius comes from the increase of the concentration of tracers at the interface. Indeed, as shown in FIG. 6a, for layers of constant area but different volumes $V_L$ and identical molar flow rates $Q_a$ of a given surfactant, the radius $r_t$ starts to decrease at the same time independently of $V_L$. It has to be noted that the thickness of the layer influences the kind of flow observed when it becomes much thinner than 10$^{-2}$ m. In contrast, as shown in FIG. 6b, a change of the size $R_c$ of the air/water interface at constant volume leads to a significant change of the time at which decrease is observed. For the largest interfaces, it was not even observe a decrease as sharp as the one noticed for the smallest container. This result implies that it is the coverage in tracers of the interface that matters to understand the decrease in radius observed at short times.

The Radius of the Transparent Zone as a Function of time and Concentration

As reported in FIG. 7a, the size of the transparent zone decreases first because of the packing of the tracers on the interface: this phenomenon occurs here around t=100 s. At very long times, here t~500 s, the radius $r_t$ of the transparent zone formed during the spreading of the surfactants with the longest chain used (hexadecyltrimethylammonium chloride, C$_{16}$TAC) decreases a second time, more sharply. As reported in FIG. 7b, as the surfactant molar flow rate $Q_a$ is known, it can be computed the average concentration c of surfactants of the ultra-pure layer at time t: $c=Q_a t/V_L$. Then c is rescaled by the critical micellar concentration cmc of the surfactants, equal to 1.6×10$^{-3}$ M for C$_{16}$TAC. The radius $r_t$ decreases much faster when c>0.2 cmc, a concentration above which the interfacial tension of solutions of the same surfactants starts to decrease faster as the concentration of surfactants is increased. This result indicates that the decrease of $r_t$ observed at long times is related to a decrease of the magnitude of the difference between the interfacial tension of the layer of water, that now contains surfactants, and the solution of surfactants being injected.

Measurement of the Velocity Field

Movies were used to measure the velocity field in the transparent zone and its close surroundings. The experiments were carried out with a aqueous solution containing 260 mM sodium decyl sulphate (SDeS) seeded with olive oil droplets. The surfactant molar flow rate is Qa=0.78×10–6 mol·s–1. The tracers can clearly be seen on the movies recorded.

The Influence of Viscosity on the Radius of the Transparent Zone

As reported in figure S5, equation (7) predicts that the radius of the transparent zone should increase with an increase of the viscosity $\eta_L$ of the fluid forming the layer. This prediction was tested by adding glycerol to both the layer and the continuous phase of the emulsion. From the results shown on FIG. 2c, it was known that a change in the formulation of the emulsion (such as adding more oil, and hence changing the viscosity of the emulsion) does not change the value taken by the radius of the transparent zone for equal surfactant molar flow rates. In contrast, the data presented here show that an increase of the viscosity of the layer at constant flow rate and with identically formulated emulsions leads to an increase of the radius $r_t$ of the transparent zone.

These results thus support the fact that our model captures very well the physics of the Marangoni flow induced by hydrosoluble surfactants over thick layers very well. Data obtained with an aqueous solution of sodium dodecyl sulphate (SDoS, [SDoS]=120 mM) at a molar flow rate $Q_a$=0.4×10$^{-6}$ mol·s$^{-1}$.

Parameters Used in the Present Application c—concentration of surfactant
c*—solubility limit of the surfactant monomers, also known as the critical micellar concentration (cmc)
D—bulk diffusion constant of the surfactant
$d_o$—inner diameter
$d_o$—outer diameter of the steel needle
F—frame rate
h—thickness of the solvent layer
n—number of carbon atoms in the hydrocarbon chain (n and Nc are used interchangeably in the present application)
$N_c$—number of carbon atoms in the hydrocarbon chain (n and Nc are used interchangeably in the present application)
Q—Total flow rate of the solution
$Q_a$—Surfactant flow rate
r—radius of the flow
$r_e$—radius of the transparent zone ($r_e$ and $r_t$ are used interchangeably in the present application)
$r_{eff}$—effective radius during micellization $r_s$—radius of the source
$r_t$—radius of the transparent zone ($r_e$ and $r_t$ are used interchangeably in the present application)
$r_{t,max}$ (or $r_{e,max}$)—maximum radius of the transparent zone
$r^*$—distance over which radial velocity gradients are established
Sc—Schmidt number
t—time
u—velocity of the transparent zone
$u_{max}$—maximum velocity of the transparent zone
$u^*$—a characteristic velocity at the interface
U—
v—kinetic viscosity
$V_a$—Volumes of surfactant solution
$V_0$—Volume of oil ($V_0$ and $V_{Oil}$ are used interchangeably in the present application)
$V_{Oil}$—Volume of oil ($V_0$ and $V_{Oil}$ are used interchangeably in the present application)
$\gamma_s$—surface tension of the (surfactant) solution
$\gamma_w$—surface tension of ultra-pure water
$\Delta\gamma$=gradient of interfacial tension ($\Delta\gamma$ ou $\Pi$, which are used interchangeably in the present application, equals $\gamma_s-\gamma_w$)
$\eta$=dynamic viscosity of the liquid
$\theta$=ratio
$\Pi$=The surface pressure ($\Delta\gamma$ ou $\Pi$, which are used interchangeably in the present application, equals $\gamma_s-\gamma_w$)
$\rho$=density of the liquid
$\sigma$—resistivity Abbreviations Used in the Present Application DeTAB ou $C_{10}TAB$—decyl trimethylammonium bromide
DoTAB ou $C_{12}TAB$—dodecyl trimethylammonium bromide
DoTAC ou $C_{12}TAC$—dodecyl trimethylammonium chloride
HTAC ou $C_{16}TAC$—hexadecyl trimethylammonium chloride
SDS ou $C_{12}NaSO_4$—sodium dodecyl sulfate
SDeS ou $C_{10}NaSO_4$—sodium decyl sulfate
SOS $C_8NaSO_4$—sodium octyl sulfate
$\Pi$ AB ou $C_{14}TAB$—tetradecyl trimethylammonium bromide

The invention claimed is:

1. A method for assessing the critical micellar concentration of amphiphilic compounds comprising the steps of:
   providing a solvent;
   preparing a layer of solvent;
   preparing and providing a solution comprising amphiphilic compounds;
   dispersing tracing particles into the solution;
   injecting the traceable solution at a surface of the solvent layer, upon injection of the traceable solution at the surface of the solvent layer at a constant total flow rate Q;
   taking pictures of the surface of the solvent layer, upon injection of the traceable solution, and determining a radius re of a corona formed;
   assessing a velocity u of the tracing particles dispersed into the traceable solution, preferably upon injection of said solution to the surface of the solvent layer, and determining a maximum velocity umax of the tracing particles; and
   from these measurement and using an associated model, determining the critical micellar concentration of the amphiphilic compounds,
   wherein the critical micellar concentration is assessed using two scaling laws:

$$u^* \propto A[(\gamma w-\gamma s)2/(\eta\rho r)]1/3,$$

$$r^* \propto B[(\eta\rho)/(\gamma w-\gamma s)2D3]1/8\cdot(Qa/c^*)^{3/4},$$

wherein $u^*$ is the velocity of the transparent zone, A is a prefactor, $\gamma w$ is the surface tension of ultra-pure water, $\gamma s$ is the surface tension of the surfactant solution, $\eta$ is the dynamic viscosity of the liquid, p is the density of the liquid, $r^*$ is the radius of the transparent zone, Qa is the surfactant flow rate of the solution, D is the bulk diffusion constant of the surfactant, and $c^*$ is the solubility limit of the surfactant monomers, also known as the critical micellar concentration (cmc).

2. A method, according to claim 1, wherein:
   the layer of solvent is a few centimeters thick;
   the solution comprising amphiphilic compounds is a solution of surfactant which is to be tested in the same solvent;
   the tracing particles follow the flow;
   the traceable solution is a particle-seeded surfactant solution which is infected at the surface of the solvent layer at a constant flow rate Q using a pump;
   the pictures of the surface of the layer allow the measurement and determination of the the radius re of the corona formed;
   the velocity of the tracing particles is tracked either through high speed imaging or with other velocimetric techniques, and from this measurement, the maximum velocity of the tracers is extracted;
   the critical micellar concentration of the amphiphilic compounds is determined by plotting the velocity against the radius, and from this measurement, the physicochemical properties of the amphiphiles are deduced, wherein the physicochemical properties comprise the critical micellar concentration.

3. A method, according to claim 1, wherein it further comprises the step of measuring the surface tension $\gamma s$ of the solution.

4. A method, according to claim 1, wherein the solvent for preparing the solvent layer is water.

5. A method, according to claim 1, wherein the solvent layer has a thickness h ranging from 1 cm to 10 cm.

6. A method, according to claim 1, wherein the solution comprises amphiphilic compounds selected from the group consisting of: lipids, soaps, and surfactants.

7. A method, according to claim 1, wherein the solution comprises a concentration c of amphiphilic compounds ranging from 5 to 15 times the critical micellar concentration.

8. A method, according to claim 1, wherein the solution comprises water, as solvent.

9. A method, according to claim 1, wherein the tracing particles are selected from the group consisting of oils.

10. A method, according to claim 1, wherein the traceable solution comprises from 30% to 60% of tracing particles when compared to the total volume of the solution.

11. A method, according to claim 1, wherein the traceable solution is injected at the surface of the solvent layer at a total constant flow rate Q ranging from 1 to 10 micromole/s.

12. Device for assessing the critical micellar concentration of amphiphilic compounds according to the method of claim 1, comprising:
   a container, for storing the traceable solution comprising amphiphilic compounds;
   a tank, for containing the solvent layer;

an injection means, connected to the storage container, and located over the tank, wherein the injection means is suitable for injecting the traceable solution at the surface of the solvent layer;

a pumping means, for assisting the injection of the traceable solution at the surface of the solvent layer;

an image-recording apparatus, for recording movies, taking pictures, or both, of the surface of the solvent layer, upon injection of the traceable solution;

an image-processing apparatus, for processing the taken images, recorded movies, or both obtained with the image-recording apparatus; and a computer for measuring the physicochemical parameters of the amphiphilic compounds.

13. The method of claim 5, wherein the solvent layer has a thickness h ranging from 2 cm to 4 cm.

14. The method of claim 5, wherein the solvent layer has a thickness h ranging from around 10-2 m.

15. The method of claim 7, wherein the solution comprises a concentration c of amphiphilic compounds 10 times the critical micellar concentration.

16. The method of claim 10, wherein the traceable solution comprises from 40% to 50% of tracing particles when compared to the total volume of the solution.

17. The method of claim 3, further comprising the step of measuring the surface tension of the solvent layer γs of the solution, by measuring the gradient Δγ of surface tension between the solvent layer and the traceable solution.

18. The method of claim 4, wherein the solvent for preparing the solvent layer is water substantially free of amphiphilic compounds.

\* \* \* \* \*